United States Patent
Kwetkat et al.

(10) Patent No.: US 6,323,363 B1
(45) Date of Patent: Nov. 27, 2001

(54) AMPHIPHILIC COMPOUNDS WITH AT LEAST TWO HYDROPHILIC AND AT LEAST TWO HYDROPHOBIC GROUPS BASED ON DICARBOXYLIC ACID DIAMIDES

(75) Inventors: Klaus Kwetkat, Bergkamen; Ulrike Jacobs, Haltern; Silvia Scholz, Zum Blickpunkt, all of (DE)

(73) Assignee: RWE-DEA Aktiengesellschaft fuer Mineraloel und Chemie (DE)

( * ) Notice: Subject to any disclaimer, the term of this patent is extended or adjusted under 35 U.S.C. 154(b) by 0 days.

(21) Appl. No.: 09/242,547

(22) PCT Filed: Jul. 19, 1997

(86) PCT No.: PCT/EP97/03933

§ 371 Date: Feb. 18, 1999

§ 102(e) Date: Feb. 18, 1999

(87) PCT Pub. No.: WO98/07689

PCT Pub. Date: Feb. 26, 1998

(30) Foreign Application Priority Data

Aug. 20, 1996 (DE) .............................. 196 33 497

(51) Int. Cl.$^7$ .................................. C07C 309/00
(52) U.S. Cl. .............................. 562/101; 554/94; 554/96; 554/97; 560/149; 560/151; 558/30; 562/102
(58) Field of Search .................. 554/94, 96, 97; 560/149, 151; 562/106, 101, 102; 558/30

(56) References Cited

U.S. PATENT DOCUMENTS

| | | | |
|---|---|---|---|
| 2,028,091 | 1/1936 | Jaeger | 560/151 |
| 2,192,906 | 3/1940 | Hanford et al. | 558/30 |
| 3,246,023 | 4/1966 | Shen et al. | 554/96 |
| 5,160,450 | 11/1992 | Okahara et al. | 510/467 |

FOREIGN PATENT DOCUMENTS

| | | |
|---|---|---|
| 3932492 | 5/1991 | (DE) . |
| 1464243 | 12/1966 | (FR) . |
| 1304033 | 12/1989 | (JP) . |
| 4124165 | 4/1992 | (JP) . |
| 07003287 | 1/1995 | (JP) . |
| WO 96/25393 | 8/1996 | (WO) . |

OTHER PUBLICATIONS

Chemical Abstracts 98:98705: Kashlinskaya, P.E.; Verezhnikov, V.N.; and Goncharova, N.I.: "Study of the Interaction of Gelatin and Surface–Active Agents by Turbidimetry," Kolloidn. Zh., 44(6), 1982, pp. 1170–1173.

Chemical Abstracts 107:200971: Kudryashova, L.M.; Trokhachenkova, O.P.; Bondarevskaya, E.A., "Atomic Absorption Determination of Sodium and Silicon in Organosilicon and Organofluorosilicon Surfactants," Zh. Anal. Khim. 42(6), 1987, pp. 1036–1040.

Zana, R.; Benrraou, M.; Rueff, R., Alkanediyl–a, w–bis–(*dimethylalkylammonium bromide*) Surfactants. 1. Effect of the Spacer Chain Length on the Critical Micelle Concentration and Micelle Ionization Degree. Langmuir 7, 1991, pp. 1072–1075.

Alami, E.; Beinert, G.; Marie, P.; Zana, R., Alkanediyl–a, w–bis ( *dimethylalkylammonium bromide*) Surfactants. 3. Behavior at the Air–Water Interface. Langmuir 9, 1993, pp. 1465–1467.

Zana, R.; Talmon, Y., "Dependence of Aggregate Morphology on Structure of Dimeric Surfactants," Nature 362, Mar. 18, 1993, pp. 228–230.

*Primary Examiner*—Paul J. Killos
*Assistant Examiner*—Taylor V Oh
(74) *Attorney, Agent, or Firm*—Browning Bushman

(57) ABSTRACT

The invention concerns amphiphilic compounds of general formula (I)

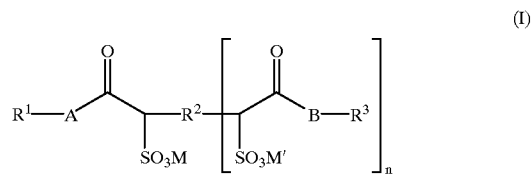

(I)

with at least two hydrophilic and at least two hydrophobic groups based on dicarboxylic acid diamides. The disclosed amphiphilic compounds mostly have a surfactant activity and are useful as emulsifiers, demulsifiers, detergents, dispersants, and hydrotropic agents for industry and household, for example in the fields of metal working, ore mining, surface finishing, washing and cleaning, cosmetics, medicine, foodstuff processing and preparation.

6 Claims, No Drawings

AMPHIPHILIC COMPOUNDS WITH AT LEAST TWO HYDROPHILIC AND AT LEAST TWO HYDROPHOBIC GROUPS BASED ON DICARBOXYLIC ACID DIAMIDES

This invention relates to amphiphilic compounds having at least two hydrophilic and at least two hydrophobic groups based on dicarboxylic acid diamides.

A wide variety of anionic, cationic, nonionic, and zwitterionic compounds are known as amphiphilic substances. Most of these substances comprise a hydrophilic head group and at least one hydrophobic moiety.

For ecological reasons, for instance regarding the demand for reduced packaging and transportation expenditure, there is a necessity for increasing the efficiency per mass of amphiphilic substance used. Since only little optimization can be achieved by mixing amphiphilic substances, there exists a need for novel amphiphilic substances having higher efficiencies. In particular, there is a need for substances having lower critical micelle concentrations and/or lower surface and interfacial tension in order to significantly reduce the amount of agent used.

Several routes to solving this problem by doubling part of the structure (hydrophilic head group, hydrophobic group) are known in the art. For example, it is known to prepare cationic surface-active compounds by addition of long-chain alkyl halides to permethylated alkylene diamines [see Zana, R., Benrraou, M., Rueff, R., Langmuir, 7 (1991), p. 1072; Zana, R., Talmon, Y., *Nature,* 362 (1993), p. 228; Alami, E., Beinert, G., Marie, P., Zana, R., Langmuir, 9 (1993), p. 1465].

Anionic surface-active compounds having at least two hydrophilic and at least two hydrophobic groups were prepared on the basis of diglycidyl ethers (cf. U.S. Pat. No. 5,160,450, JP 01 304 033, JP 4 124 165). However, diglycidyl ethers are rated as toxicologically critical and are rather expensive. Furthermore, said compounds are manufactured using epichlorohydrin. This method results in the production of large amounts of residues so that said compounds are obsolete both under ecotoxicological and economic aspects.

A large number of esters of α-sulfocarboxylic acids and polyalkylene oxide glycol ethers, also including amphiphilic compounds, have been described in U.S. Pat. No. 3,246,023. Said compounds are reported to be of nearly universal use, e.g. as emulsifiers for insecticides, pesticides and herbicides, as additives to petroleum products and rubber latices, as foam inhibitors, auxiliaries for road-building materials and for making concrete or paper, as mercerizing assistants, corrosion inhibitors, additives to cosmetic preparations, and, generally, as cleansing agents in hard water.

Therefore, it was an object of the present invention to find amphiphilic compounds having at least two hydrophilic and at least two hydrophobic groups, wherein the amphiphilic compounds are highly efficient, referring to the feed quantity, and, furthermore, can be prepared from technically readily available raw materials without producing large amounts of undesired by-products.

According to the present invention, the problem is solved by providing amphiphilic dicarboxylic acid diamides the basic structures of which can be prepared from dicarboxylic acids or esters thereof and alkyl amines. The corresponding amides can be sulfonated and subsequently neutralized.

The amphiphilic compounds of this invention are compounds having the general formula I

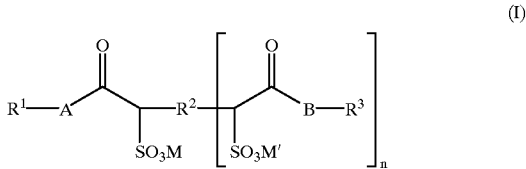

where $R^1$, $R^3_1$ and $R^3$ in formula I are defined as set forth hereinbelow:

$R^1$ and $R^3_1$ independently, represent an unbranched or branched, saturated or unsaturated hydrocarbon residue having 8 to 22 carbon atoms. For instance, the substituents $R^1$ and $R^3$ may be the residues n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-henicosyl, n-docosyl, and branched-chain isomers thereof as well as the corresponding mono-, twofold, or threefold unsaturated residues.

The spacer $R^2$ represents unbranched or branched alkylene chains of formula II

where a is equal to from 2 to 18, preferably 2 to 6; alicyclic compounds of formula IV

where each f and g, independently, is equal to from 1 to 6;

optionally, substituted aromatics of formula VI

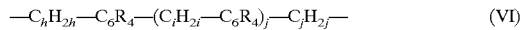

or of formula VII

where each h and j, independently, is equal to from 0 to 8 and i is equal to from 0 to 8 and each R, independently, is equal to H or $C_1$ to $C_6$ alkyl.

Letter n in formula I represents the number 1.

In addition, $R^2$ may be derived from a methyl or ethyl ester of a polycarboxylic acid (molecular weight from 500 to 100,000, preferably from 500 to 1,000) the α-carbon atoms of which have a sulfonation degree of from 0 to 100%, preferably 10 to 60%. In this case n is in the range of from 1 to 25,000.

M and M' represent alkali, ammonium, alkanol ammonium, or ½ alkaline earth ion.

A and B, independently, are —NH—, $NR^4$— (where $R^4$ is equal to methyl, ethyl, propyl, butyl, or methoxyethyl, methoxypropyl, ethoxypropyl), —N($R^5$)—O($C_2H_4O$)$_\alpha$($C_3H_6O$)$_\beta$— (where α is equal to from 0 to 20, preferably 0 to 10, and β is equal to from 0 to 20, preferably 0 to 10, and α and β cannot be simultaneously 0, and $R^5$ is equal to $R^4$ or to —O($C_2H_4O$)$_\alpha$($C_3H_6O$)$_\beta$—H under the conditions set forth hereinabove), or —C(O)N($R^5$)—O($C_2H_4O$)$_\alpha$($C_3H_6O$)$_\beta$— under the conditions set forth hereinabove.

The outstanding characteristics of most of the amphiphilic compounds of the present invention are their extremely low critical micelle concentrations (CMC) and very low surface/interfacial tensions, e.g. in contact with paraffin. Said properties are due to the special structures of the compounds, namely at least two hydrophilic and at least two hydrophobic groups.

Furthermore, most of said compounds have rather high hydrophilic suspending power which is rated to be halfway between that of conventional surfactants and pentasodium tripolyphosphate. Some of said compounds have extremely high wetting activities. Salts of sulfonated esters of unsaturated dicarboxylic acids with unsaturated fatty alcohols are described in DE 39 32 492 (unexamined German patent application). However, the structures of said compounds are completely different from those of the compounds of this invention because, according to DE 39 32 492, the $SO_3$ is exclusively added to double bonds.

The amphiphilic compounds of the present invention are particularly useful as emulsifiers, demulsifiers, detergents, dispersants, and hydrotropes in industrial and domestic applications, e.g. in the fields of metal working, ore mining, surface finishing, washing and cleaning, cosmetics, medicine, foodstuff processing and preparation.

Said compounds may be employed in combination with any customary anionic, nonionic, cationic, and ampholytic surface-active substances. Examples of nonionic surface-active substances suitable for said combinations include fatty acid glycerides, fatty acid polyglycerides, fatty acid esters, ethoxylates of higher alcohols, polyoxyethylene fatty acid glycerides, polyoxyethylene propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkyl amines, alkanol amines, alkylamine oxides, protein hydrolysate derivatives, hydroxy mixed ethers, alkyl polyglycosides, and alkyl glucamides.

Examples of anionic surface-active substances useful for said combinations include soaps, ether carboxylic acids and salts thereof, alkyl sulfonates, α-olefin sulfonates, sulfonates of higher fatty acid esters, higher alcohol sulfates, alcohol ether sulfates, hydroxy mixed ether sulfates, alkanoyl and alkenoyl sarcosinates, phosphate ester salts, taurides, isethionates, linear alkyl benzene sulfonates, cumene sulfonate, alkylaryl sulfonates, polyoxyethylene fatty acid amide sulfates, and acylamino acid salts.

Examples of conventional cationic surface-active substances suitable for said combinations include alkyltrimethyl ammonium salts, dialkyldimethyl ammonium salts, alkyldimethylbenzyl ammonium salts, alkyl pyridinium salts, alkylisoquinolinium salts, benzethonium chlorides, and cationic acylamino acid derivatives.

Examples of ampholytic surface-active substances useful for said combinations include amino acids, betaines, sulfobetaines, imidazoline derivatives, soybean oil lipids, and lecithin.

Furthermore, the amphiphilic compounds of the present invention may also be combined with each other.

In addition, any commonly used additives may be added to the amphiphilic compounds of the invention. Such additives may be suitably chosen for a desired formulation and generally include inorganic salts, such as sodium chloride and sodium sulfate, builders, hydrotropes, UV absorbers, softeners, chelating agents, viscosity modifiers, fragrances, and enzymes.

The foregoing compounds can be prepared by amidation of dicarboxylic acids or esters thereof with alkyl amines and by at least twofold sulfonation of the dicarboxylic acid dialkyl amides. Either of the following two methods may be employed: sulfonation of dicarboxylic acid alkyl ester (with the alkyl residue having 1 to 6 carbon atoms) followed by amidation with longer-chain alkylaminopolyalkoxylates or alkylamines, or sulfonation of the completed basic structure, the first method being preferred.

Aqueous alkali hydroxides or alkaline earth hydroxides or aqueous ammonia or alkanol amines are used for the neutralization. Optionally, the products can be bleached in substance or, preferably, in aqueous solution with hydrogen peroxide (0.1 to 2.0 %, referring to the solid material).

What is claimed is:
1. Amphiphilic compounds having the general formula I:

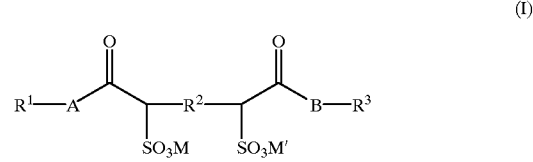

(I)

wherein:
  $R^1$ and $R^3$, independently, are an unbranched or branched, saturated or unsaturated hydrocarbon residue having 8 to 22 carbon atoms,
  $R^2$ is (1) an unbranched or branched alkylene chain of formula II:

(II)

wherein a is equal to from 2 to 18 or
  $R^2$ is (2) an alicyclic compound of formula IV:

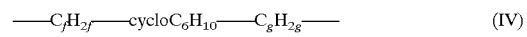

(IV)

wherein each f and g, independently, is equal to from 1 to 6 or
  $R^2$ is (3) an unsubstituted or substituted aromatic compound of formula VI:

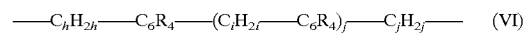

(VI)

or of formula VII:

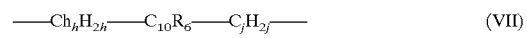

(VII)

wherein each h and j, independently, is equal to from 0 to 8 and i is equal to from 0 to 8 and each R, independently, is equal to H or $C_1$ to $C_6$ alkyl or
  $R^2$ is (4) derived from a methyl or ethyl ester of a polycarboxylic acid with a molecular weight of 500 to 100,000 wherein the α-carbon atoms of which have an average sulfonation degree of from greater than 0 to 100%,
  M and M' represent an alkali, ammonium, alkanol ammonium, or ½ alkaline earth ion, and
  A and B, independently, are ——NH——, —NR— or —N($R^5$)—O($C_2H_4O)_\alpha(C_3H_6O)_\beta$ or —C(O)N($R^5$)—O—($C_2H_4O)_\alpha(C_3H_6O)_\beta$—
  wherein
  $R^4$ is equal to methyl, ethyl, propyl, butyl, or methoxyethyl, methoxypropyl or ethoxypropyl and
  $R^5$ is equal to $R^4$ or —O($C_2H_4O)_\alpha(C_3H_6O)_\beta$—H under the conditions set forth hereinabove, and
  the sum of α and β is 1 or greater.

2. The amphiphilic compounds of claim 1 wherein a is from 2 to 6.

3. The amphiphilic compounds of claim 1 wherein the α-carbon atoms have a sulfonation degree of from 10 to 60%.

4. A composition of matter comprising an amphiphilic compound according to claim 1 and a second compound selected from the group consisting of anionic, nonionic, cationic, and ampholytic surface-active substances.

5. The composition of claim 4 wherein a is from 2 to 6.

6. The composition of claim 4 wherein the α-carbon atoms have a sulfonation degree of from 10 to 60%.

* * * * *

UNITED STATES PATENT AND TRADEMARK OFFICE
CERTIFICATE OF CORRECTION

PATENT NO. : 6,323,363 B1
DATED : November 27, 2001
INVENTOR(S) : Klaus Kwetkat, Ulrike Jacobs and Silvia Scholz It is certified that error appears in the above-identified patent and that said Letters Patent is hereby corrected as shown below:

<u>Column 4,</u>
Line 46, delete "$Ch_hH_{2h}$" and insert -- $C_hH_{2h}$ --.
Line 58, delete "NR" and insert -- $NR^4$ --.

Signed and Sealed this

Nineteenth Day of March, 2002

JAMES E. ROGAN
*Director of the United States Patent and Trademark Office*

*Attest:*

*Attesting Officer*